(12) United States Patent
Shim et al.

(10) Patent No.: US 8,409,623 B2
(45) Date of Patent: Apr. 2, 2013

(54) CANCELLOUS BONE GRAFT SUBSTITUTE AND METHOD OF MANUFACTURING THE SAME

(75) Inventors: Young Bock Shim, Seoul (KR); Ju Woong Jang, Seoul (KR); Hyang Kim, Gyeonnggi-do (KR); Kwang Il Lee, Gyeonggi-do (KR); Keun Soo Lee, Gangwon-do (KR); Il Hwan Kim, Seoul (KR)

(73) Assignee: Korea Bone Bank, Inc., Seoul (KR)

( * ) Notice: Subject to any disclaimer, the term of this patent is extended or adjusted under 35 U.S.C. 154(b) by 891 days.

(21) Appl. No.: 12/359,125

(22) Filed: Jan. 23, 2009

(65) Prior Publication Data

US 2010/0166879 A1    Jul. 1, 2010

(30) Foreign Application Priority Data

Dec. 31, 2008    (KR) .................. 10-2008-0138644

(51) Int. Cl.
*A61K 35/32*    (2006.01)
(52) U.S. Cl. .................. 424/549; 264/405; 264/442
(58) Field of Classification Search .................. None
See application file for complete search history.

(56) References Cited

U.S. PATENT DOCUMENTS

| 5,474,555 | A | 12/1995 | Puno | |
| 5,797,871 | A * | 8/1998 | Wolfinbarger, Jr. | 604/500 |
| 6,534,095 | B1 * | 3/2003 | Moore-Smith et al. | 424/549 |
| 2003/0135284 | A1 * | 7/2003 | Crouch et al. | 623/23.61 |
| 2008/0305145 | A1 | 12/2008 | Shelby | |

FOREIGN PATENT DOCUMENTS

KR    2002-0011164 A    2/2002

OTHER PUBLICATIONS

Oh et al., Cryobiology, 2002, vol. 44, p. 279-287.*

* cited by examiner

*Primary Examiner* — Kade Ariani
(74) *Attorney, Agent, or Firm* — Christensen O'Connor Johnson Kindness PLLC

(57) ABSTRACT

A cancellous bone graft substitute and a method of manufacturing the cancellous bone graft substitute are provided, and more particularly, a cancellous bone graft substitute and a method of manufacturing the cancellous bone graft substitute by which defatting, demineralizing, cleaning, and sterilizing processes are performed within a short time using a supersonic cabitation without damaging a surface and an inside of a bone tissue so as to further rapidly, effectively supply an allogeneic or xenogeneic bone graft substitute. Internal and external concentrations of Ca++ of the allogeneic or xenogeneic bone graft substitute are effectively removed so as to maintain physical properties of the allogenetic or xenogeneic bone graft substitute.

7 Claims, 4 Drawing Sheets

(A)

<PRIOR ART>

(B)

CANCELLOUS BONE GRAFT SUBSTITUTE AND METHOD OF MANUFACTURING THE SAME

BACKGROUND

The present invention relates to a cancellous bone graft substitute and a method of manufacturing the same, and more particularly, to a cancellous bone graft substitute and a method of manufacturing the same by which defatting, demineralizing, cleaning, and sterilizing processes are performed within a short time using a supersonic cavitation without damaging a surface and an inside of a bone tissue so as to further rapidly, effectively supply an allogeneic or xenogeneic bone graft substitute, internal and external concentrations of Ca++ of the allogeneic or xenogeneic bone graft substitute are effectively removed so as to maintain physical properties of the allogeneic or xenogeneic bone graft substitute, such as an elastic intensity and the like, osteogenesis induction factors of a demineralized bone matrix (DBM), such as bone morphogenetic proteins (BMPs), growth factors, and proteoglycan, are protected so as to effectively grow the osteoinductive factors, and a protectant is applied to the allogeneic or xenogeneic bone graft substitute so as not to easily dissolve or inactivate the allogeneic or xenogeneic hone graft substitute.

Bone grafts are applied to fill spaces of bone tissues, which are damaged by bone diseases such as bone troubles, bone tumors, and the like, with bone graft substitutes or to induce bone joints, bone integrations, and joint fixations. The development and necessity of industrialization and medical science have been expanded with an increase in an aged population and the qualitative improvement of lives. Thus, researches on simpler, more effective bone cure graft substitutes have been actively conducted in order to cope with the development and necessity of industrialization and medical science.

The most generally used bone graft method is a self-graft method of extracting a part of a bone of a graftee in order to implant the extracted part to a damaged part of the bone. If an autogenous cancellous bone (ACB) is implanted to a damaged part as described above, alive cells related to a bone matrix and osteogenesis are supplied to a graft part. Thus, the ACB more rapidly generate a bone than other graft substitutes, hardly causes an immune rejection response, and does not cause osteoclasis so as to improve osteoconductive and osteoinductive capabilities.

However, since a graft substitute is extracted from a graftee in the above-described self-graft method, a surgical operation must be performed with respect to a damaged part of a bond and a part from which the graft substitute has been extracted. Also, an amount of the graft substitute obtained from the graftee is very limited.

Therefore, an allograft using a bone of another person not a graftee or a xenograft (Mulliken et al., Calcif. Tissue Int. 33:71, 1981; Neigel et al., Opthal. Plast. Teconstr. Surg. 12:108, 1996; Whiteman et al., J. Hand. Surg. 18B: 487, 1993; Xiaobo et al., Clin. Orthop. 293:360, 1993) using a bone of an animal has been developed in order to solve the above-mentioned problems of the self-graft method. With the development of the allograft and the xenograft, an allogeneic or xenogeneic demineralized bone matrix (DBM) has been developed in order to remove cells, blood, a lipid layer, and the like, which causes an immune rejection response, from a graft substitute and activate osteoinductive BMPs which participate in osteoinduction.

The allogeneic or xenogeneic demineralized DBM does not require a secondary operation for extracting a graft substitute, is demineralized (i.e., is easily processed) to be appropriate for characteristics of a graftee, and smoothly supply a graft substitute. In order to manufacture such a DBM, an allogeneic or xenogeneic bone is cleaned, defatted, antisepticized, and/or sterilized in order to remove infectious viruses, is cut using micromachining, and is soaked in an acid solution.

However, a well-known method of manufacturing an allogeneic or xenogeneic DBM requires a considerable amount of time in order to manufacture the allogeneic or xenogeneic DBM. Also, since graft substitutes, which are manufactured and commercialized by the well-known method, are rapidly dissolved after being implanted, they considerably reduce an osteoinductive activation within 24 hours after the implantation. Also, some of the graft substitutes are inactivated within 6 hours after the implantation and thus lose their osteoconductive and osteoinductive capabilities.

This is because general vacuum freeze drying is performed in order to supply bone graft substitutes at appropriate times. Since the vacuum freeze drying repeats freezing and dehydrating, biomechanical characteristics of a bone tissue are deteriorated, which damages the bone graft substitutes. Also, when gamma radioactive rays are irradiated as an alternative to the vacuum freeze drying or the vacuum freeze drying and the irradiation of gamma radioactive rays are simultaneously used, the damages to the bone graft substitutes are amplified.

Accordingly, with the increases in usage of bone graft substitutes, there is required to be developed a method of further simply, rapidly supplying a high-quality allogeneic or xenogeneic cure bone graft substitute and effectively complementing a damage to the bone graft substitute which is caused during the manufacture of the bone graft substitute.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one aspect of an embodiment, a cancellous bone graft substitute and a method of manufacturing the same are provided. In some embodiments, ethanol processing, peroxide processing, and demineralization processing are performed using a supersonic cavitation in order to manufacture a high-quality cancellous bone graft substitute within a short time without damaging a surface and an inside of a bone tissue.

In accordance with another aspect of an embodiment, a cancellous bone graft substitute and a method of manufacturing are provided where allogeneic or xenogeneic bone particles are demineralized and processed using a protectant so as to supply a high-quality cancellous bone graft substitute which is not easily inactivated after being implanted into a living body.

In accordance with yet another aspect of an embodiment, there is provided a method of manufacturing a cancellous bone graft substitute, including: cutting an extracted allogeneic or xenogeneic bone tissue into block patterns and removing a soft tissue; defatting, dehydrating, and deinsfecting the allogeneic or xenogeneic bone tissue using an ethanol aqueous solution; removing a residual tissue from the allogeneic or xenogeneic bone tissue which has been defatted, dehydrated, and deinsfected; deinsfecting and oxidizing the allogeneic or xenogeneic bone tissue using a peroxide; cutting the allogeneic or xenogeneic bone tissue, which has been disinfected and oxidized, into bone particles having hexahedral shapes; demineralizing the bone particles having the hexahedral shapes using a hydrochloric acid; cleaning the demineralized bone particles using an ethanol aqueous solution; neutralizing the cleaned bone particles using aphosphate buffered saline (PBS); steeping the neutralized bone particles in a RSC (Radio protective Stable Chemical) solution; cleaning and drying the bone particles which have steeped in the RSC solution; and vacuum-freeze-drying the dried bone particles.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Exemplary embodiments of the present invention will now be described in detail with reference to the attached drawings.

Figure 1:
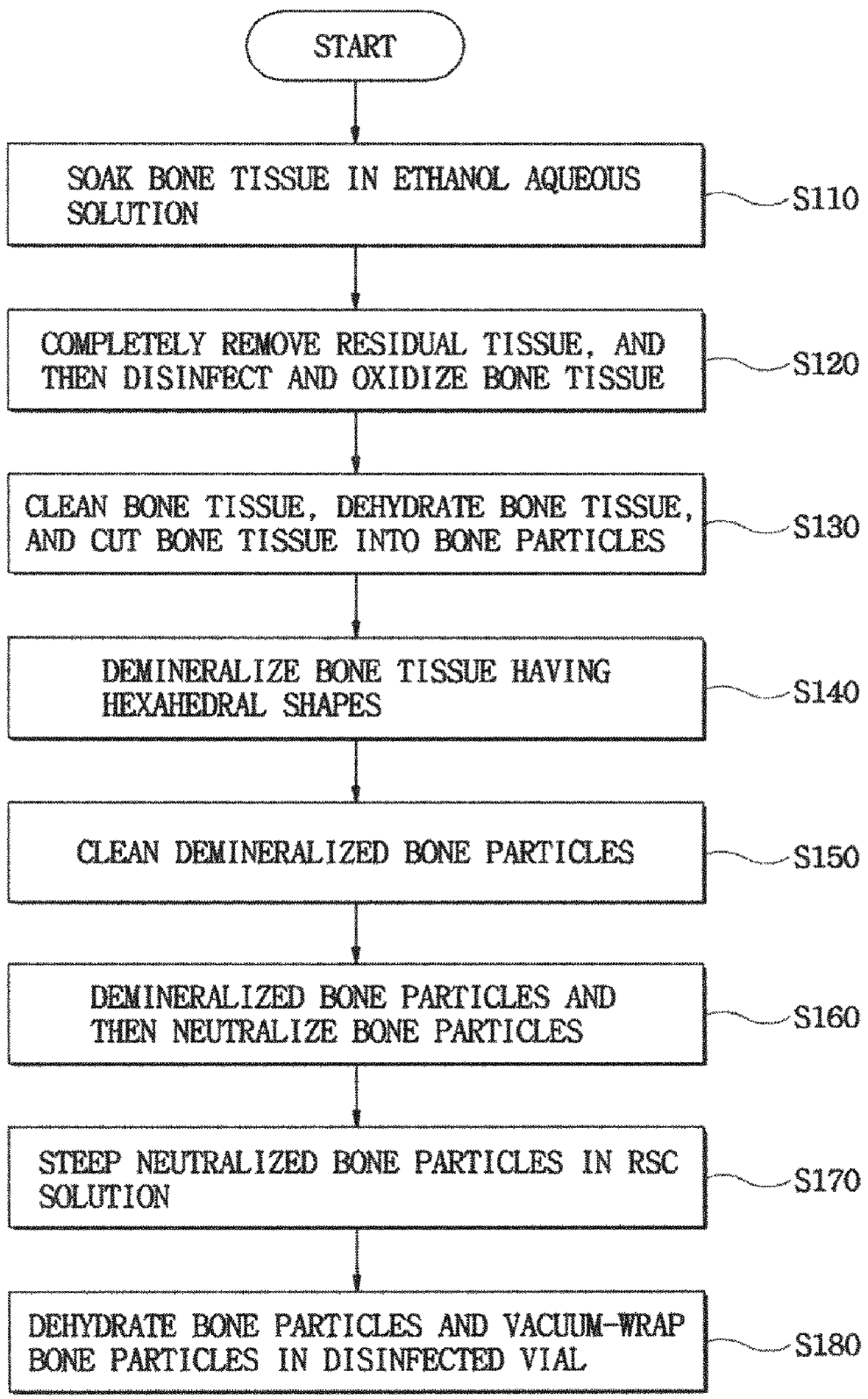
FIG. 1 is a flowchart of a method of manufacturing a cancellous bone graft substitute according to an embodiment of the present invention.

FIG. 1 is flowchart of a method of manufacturing a cancellous bone graft substitute according to an embodiment of the present invention. FIGS. 2A through 2F compare a bone tissue demineralized using a supersonic cavitation according to the present invention with a bone tissue demineralized using a general bone graft substitute manufacturing method.

A bone tissue, which has been frozen as a bone graft substitute of the present invention in a freezer of −70° C. or less, is unfrozen. The bone tissue may be an allogeneic bone which has been extracted from a dead body or a xenogeneic bone which has been extracted from an animal such as cattle, a goat, a horse, or the like.

The unfrozen bone tissue is cut in block patterns using a cutter, and then soft tissues, including fascias, connection organizations, tendons, ligaments, and the like, are removed from a surface of the bone tissue.

In operation S110, the bone tissue from which the soft tissues have been removed is soaked in an ethanol aqueous solution for about 30 minutes in order to defat, dehydrate, and disinfect the bone tissue. An optimal concentration of the ethanol aqueous solution for effectively removing lipid from the bone tissue and disinfecting the bone tissue may be 83%.

According to a conventional method of manufacturing a bone graft substitute, an ethanol aqueous solution is replaced with ones for at least 3 hours (a total of three times at least every one hour) in order to obtain a cleaned bone. However, in the method of the present invention, defatting, dehydrating, and disinfecting are optimally performed within the shortest time of about 30 minutes using a supersonic cavitation.

The supersonic cavitation refers to a phenomenon in which if a supersonic wave having a frequency of 20 KHz or more is irradiated into liquid, a medium on a path of the supersonic wave is partially heated, and thus tens of millions of microscopic bubbles are generated in the liquid and then burst due to compression. A bone tissue may be cleaned and disinfected, and lipid may be removed from a surface of the bone tissue due to energy generated when such microscopic bubbles burst in predetermined sizes or more and discharges in the microscopic bubbles.

In operation S120, a residual tissue is completely removed from the ethanol-processed bone tissue, and then the bone tissue is disinfected and oxidized in a peroxide of 3% for about 90 minutes using the supersonic cavitation by which the bone tissue has been ethanol-processed.

In the conventional method, a peroxide is replaced with one ones for about 12 hours (a total of four times at least every three hours). However, in the method of the present invention, the bone tissue can be optimally disinfected and oxidized within the shortest time of about 90 minutes.

An antigen of the surface of the bone tissue may be broken down, and bacterium and viruses may be annihilated through disinfecting using the ethanol aqueous solution, and disinfecting and oxidizing using the peroxide so as to reduce an immune rejection response of an allogeneic or xenogeneic bone graft substitute, such as a graft rejection, which occurs when the allogeneic or xenogeneic bone graft substitute is implanted into a living body.

In operation S130, the bone tissue, which has been disinfected and oxidized in the peroxide, is cleaned using purified water, dehydrated, cut into bone particles using a micromachining cutter, and classified according to size. The bone particles have hexahedral shapes, in particular, may have cubic shapes with lengths "L," widths "W," and heights "H" of 8, 10, 12, 14, or 16 mm.

In operation S140, the bone particles having the hexahedral shapes are demineralized in a hydrochloric acid (having a ratio of 15 ml/g) of 0.5N for about 30 to 90 minutes using the supersonic cavitation in order to remove inorganic mineral components from the bone particles. According to the conventional method, bone powder or bone particles are steeped in a hydrochloric acid of 0.5N in order to be demineralized for about 3 hours. However, in the method of the present invention, the bone particles can be effectively demineralized within a short time.

Figure 2A:
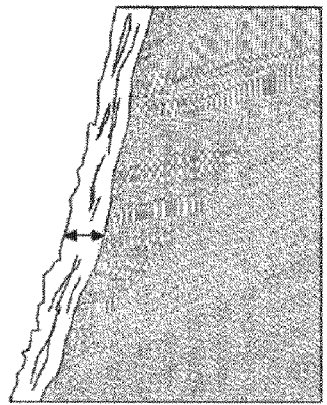
FIG. 2A through 2F compare a bone tissue demineralized using a supersonic cavitation according to the present invention with a bone tissue demineralized using a general bone graft substitute manufacturing method.
Figure 2B:
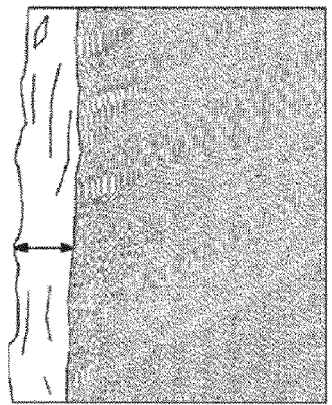
Figure 2C:
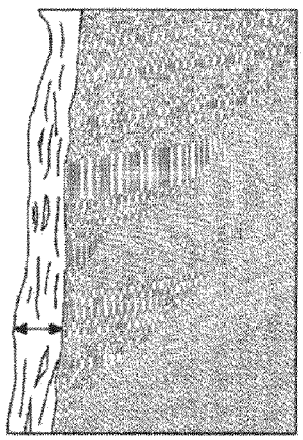
Figure 2D:
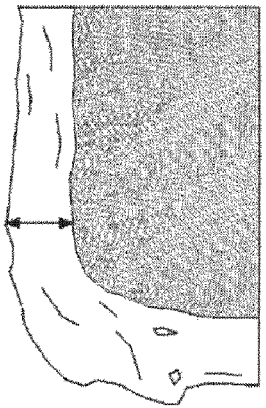
Figure 2E:
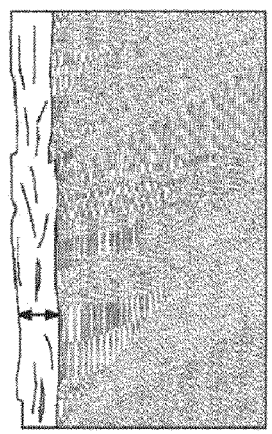
Figure 2F:
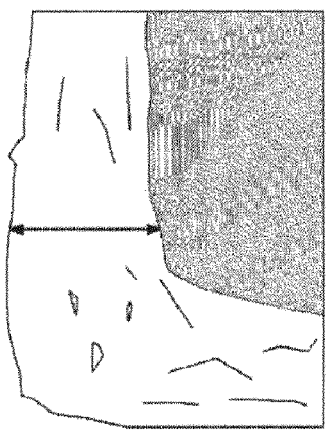

With reference to FIGS. 2A through 2F, demineralized degrees of bone particles using the supersonic cavitation according to the present invention will now be compared with demineralized degrees of bone particles using the conventional method, according to time variations. The bone particles shown in FIGS. 2A and 2B were obtained after they were demineralized in a hydrochloric acid for about 30 minutes. A surface of the hone particle shown in FIG. 2B is more demineralized than a surface of the bone particle shown in FIG. 2A. The bone particles shown in FIGS. 2C and 2D were obtained after they were demineralized in a hydrochloric acid for about 60 minutes. The bone particles shown in FIGS. 2E and 2F were after they were demineralized in a hydrochloric acid for about 90 minutes. The bone particles shown in FIGS. 2C and 2E were not greatly demineralized compared to the bone particle shown in FIG. 2A. The bone particles shown in FIGS. 2D and 2F were greatly demineralized for about 30 to 60 minutes compared to the bone particle shown in FIG. 2B.

Also, the demineralized degrees of the bone particles may be determined according to an intensity of the hydrochloric acid, shapes of pulverized bone particles, a demineralizing method, and a demineralizing time. For example, the demiernalized degrees (surface demineralizing, partial demineralizing, and complete demineralizing) of the bone particles may be controlled according to regions and fields which are to use demineralizing such as re-organization of loss of a diaphysis which is slowly cured, fixations of joints and cervical vertebrae using fixtures, cures for joints which are disintegrated and integrated by diseases and aging of femur and the like, etc.

In operation S150, the demineralized bone particles are cleaned in an ethanol aqueous solution of 83% for about 30 minutes using the supersonic cavitation. The demineralized bone particles may be more rapidly cleaned in the ethanol aqueous solution than in the conventional method by which bone particles are steeped in an ethanol aqueous solution for about 1 to 2 hours to be cleaned.

Table 1 below shows comparisons between operations S110, S120, S140, and S150 of the method of the present invention and operations of the conventional method.

The RSC solution may be formed of propylene glycol of 15 to 20%, dimethyl sulfoxide (DMSO) of 20 to 25%, mannitol of 1 to 5%, tetrahalose of 1 to 5%, and distilled water of 40 to 60%. Alternatively, the RSC solution may be formed of glycine of 15 to 20%, stachyose of 20 to 25%, mannitol of 1 to 5%, dextran of 1 to 5%, and distilled water of 40 to 60%.

Figure 3:
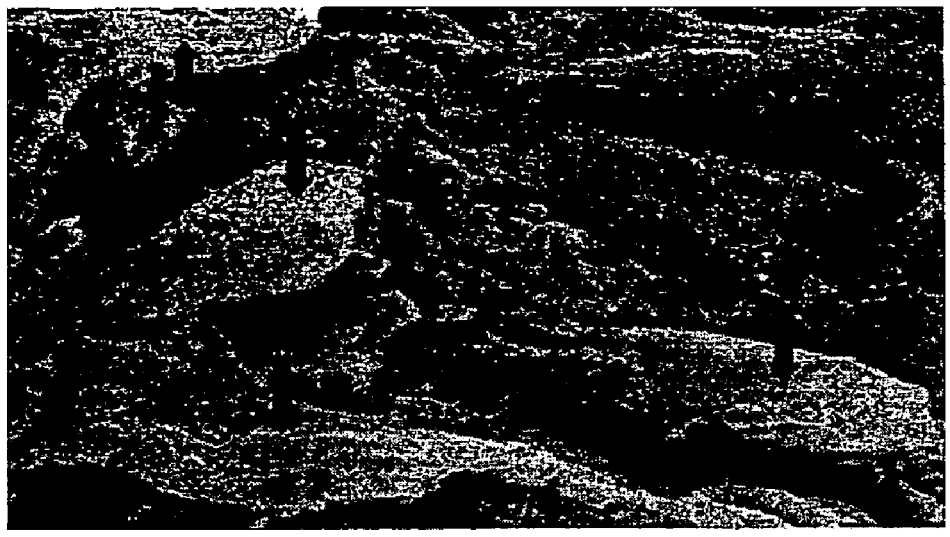
FIGS. 3A and 3B respectively illustrate a cancellous bone graft substitute according to the present invention and a general bone graft substitute which are photographed by a ×3,000-scanning electron microscope (SEM)
Figure 3:
Figure 4:
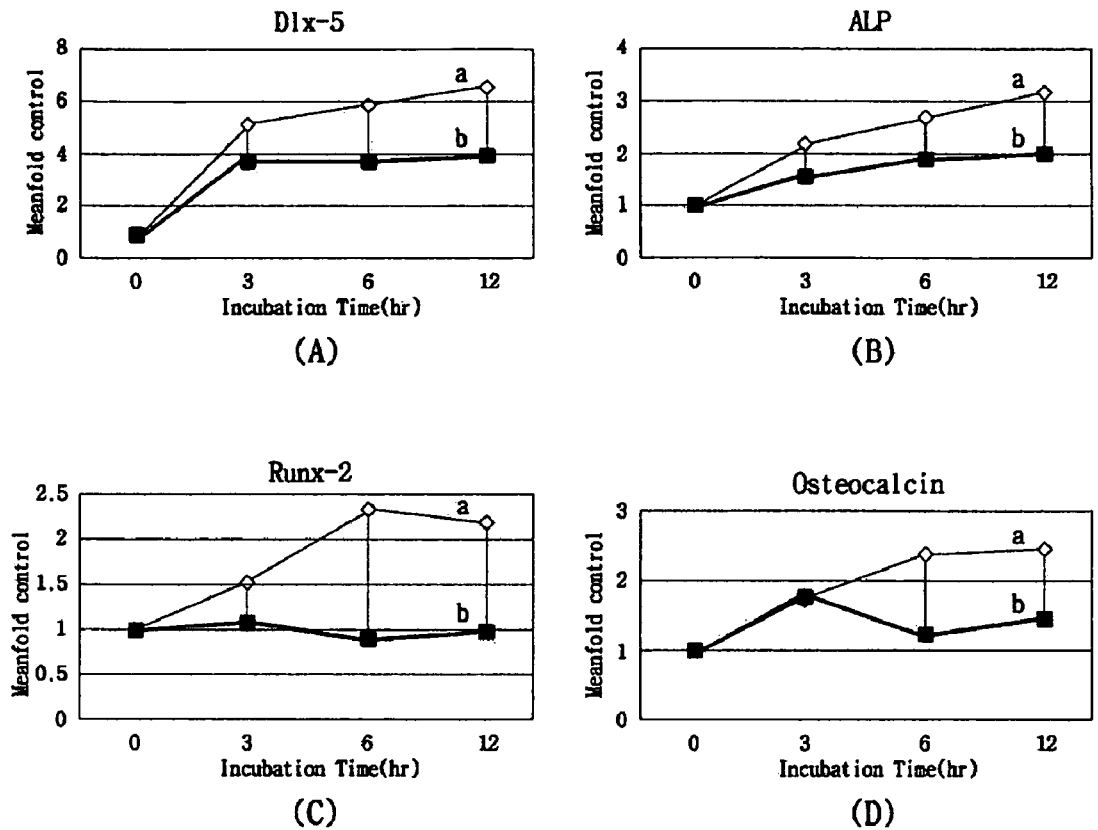
FIGS. 4A through 4D are graphs illustrating mRNA expressions of osteogenesis markers of the cancellous bone graft substitute of the present invention shown in FIG. 3A and the general bone graft substitute shown in FIG. 3B.

FIGS. 3A and 3B respectively illustrate a surface of cancellous bone graft substitute of the present invention and a surface of a general bone graft substitute which were cultured for 2 weeks and then photographed using a ×3,000-scanning electron microscope (SEM). Compared to the general bone graft substitute shown in FIG. 3B, the cancellous bone graft substitute of the present invention shown in FIG. 3A were cultured so as to form polymer including various proteins and polysaccharides and a plurality of inorganic extra cellular matrixes (ECMs) as marked with arrows. The cancellous bone graft substitute of the present invention has higher osteoconductive and osteoinductive capabilities than the general bone graft substitute.

FIGS. 4A through 4D are graphs illustrating mRNA expressions of osteogenesis markers of the cancellous bone graft substitute of the present invention shown in FIG. 3A and the general bone graft substitute shown in FIG. 3B. When osteoinduction of an osteoblast occurs due to a stimulus of an implanted bone graft substitute, osteoinductive surjection factors "Dlx-5," "ALP," "Runx-2," and osteocalcin are expressed on a DNA level. Osteoconductive and osteoinductive capabilities of a bone graft substitute can be determined according to the expression degrees of initial osteoinductive surjection factors. Horizontal axes of FIGS. 4A through 4D denote incubation time, and vertical axes of FIGS. 4A

TABLE 1

| | Conventional Method | Method of the Present Invention Using Supersonic Cabitation |
|---|---|---|
| Ethanol of 83% (S110) | About 3 Hours (Three-time Replacements of Ethanol Every 1 Hour) | About 30 Minutes (No Replacement of Ethanol) |
| Peroxide of 3% (S120) | About 12 Hours (Four-time Replacements of Peroxide Every 3 Hours | About 90 Minutes (No Replacement of Peroxide) |
| Hydrochloric Acid of 0.5N (S140) | About 3 Hours (One-time Replacement of Hydrochloric Acid) | About 30 to 90 Minutes (No Replacement of Hydrochloric Acid) |
| Ethanol of 83% (S150) | About 1 to 2 Hours (One or Two-time Replacement of Ethanol) | About 30 Minutes (No Replacement of Ethanol) |

In operation S160, the residue of an acid is removed from the cleaned, demineralized bone particles, and then the bone particles are neutralized using a phosphate buffered saline (PBS) of pH7.0 in order to increase potential of hydrogen (pH).

In operation S170, the neutralized bone particles are steeped in a RSC (Radio protective Stable Chemical) solution of 3 ml/g to be processed in a constant-temperature water bath of 40° C. for 5 hours and are processed in a freezer of 4° C. for 20 hours so as to maintain physical and active properties of the bone graft substitute including osteoconductive and osteoinductive capabilities, protect osteogenesis induction factors of a DBM, such as BMPs, growth factors, proteoglycan, and the like, and prevent the bone graft substitute from being easily dissolved or inactivated after being implanted into a living body.

The RSC solution may be formed of propylene glycol of 15 to 20%, dimethyl sulfoxide (DMSO) of 20 to 25%, mannitol of 1 to 5%, tetrahalose of 1 to 5%, and distilled water of 40 to 60%. Alternatively, the RSC solution mat be formed of glycine of 15 to 20%, stachyose of 20 to 25%, mannitol of 1 to 5%, dextran of 1 to 5%, and distilled water of 40 to 60%.

In operation S180, the bone particles arc cleaned using purified water, dehydrated, vacuum-freeze-dried for subsequent processes, and vacuum wrapped in a disinfected vial. Next, the bone particles may be capped with aluminum and then packed in a plastic box.

through 4D denote expression meanfold of a control group. The cancellous bone graft substitute of the present invention expresses the osteoinductive surjection factors "Dlx-5" and "ALP" 1.5 times the general bone graft substitute and the osteoinductive surjection factors "Runx-2" and osteocalcin about 2 times the general bone graft substitute. Thus, growth factors are actively expressed in a protein-level osteoinduction.

Figure 5:
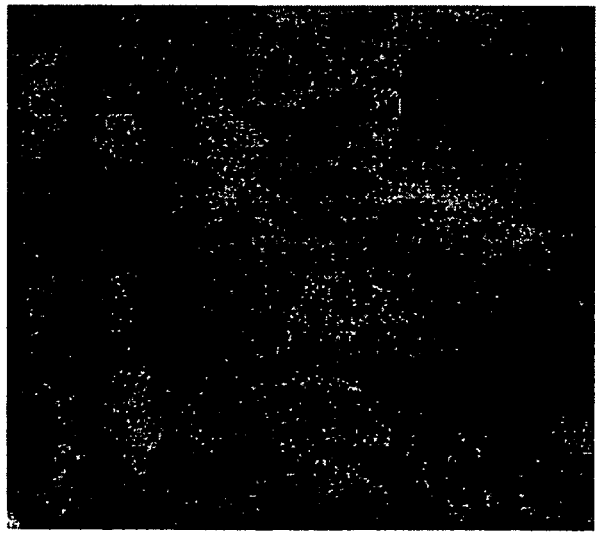
FIG. 5 illustrates a structure of a processed cancellous bone graft substitute which is photographed using a ×30 electron microscope.

FIG. 5 illustrates a processed cancellous bone graft substitute which is photographed using a ×30-electron microscope. As shown in FIG. 5, the cancellous bone graft substitute has a cancellous internal structure. Thus, the cancellous bone graft.

As described above, in a cancellous bone graft substitute and a method of manufacturing the cancellous bone graft substitute according to the present invention, a supersonic cavitation is used in order to cope with the increasing demands for bone graft substitutes so as to rapidly supply high-quality bone graft substitutes to graftees.

Also, the cancellous bone graft substitute is freeze-dried using a protectant so as to effectively induce osteogenesis without dissolving or inactivating an allogeneic or xenogeneic bone graft substitute after the allogeneic or xenogeneic bone graft substitute is implanted into a graftee.

While the present invention has been particularly shown and described with reference to exemplary embodiments thereof, it will be understood by those of ordinary skill in the art that various changes in form and details may be made therein without departing from the spirit and scope of the present invention as defined by the following claims.

The embodiments of the invention in which an exclusive property or privilege is claimed are defined as follows:

1. A method of manufacturing a cancellous bone graft substitute, comprising:
    (a) cutting an extracted allogeneic or xenogeneic bone tissue into block patterns and removing soft tissue;
    (b) defatting, dehydrating, and disinfecting the allogeneic or xenogeneic bone tissue of step (a) by adding an aqueous ethanol solution to the bone tissue and applying supersonic cavitation;
    (c) removing residual soft tissue from the allogeneic or xenogeneic bone tissue which has been defatted, dehydrated, and disinfected;
    (d) sterilizing and oxidizing the allogeneic or xenogeneic bone tissue of step (c) by adding peroxide to bone tissue and applying supersonic cavitation;
    (e) cutting the allogeneic or xenogeneic bone tissue, which has been disinfected and oxidized, into bone particles having hexahedral shapes;
    (f) demineralizing the bone particles of step (e) by adding hydrochloric acid to the bone particles and applying supersonic cavitation;
    (g) cleaning the demineralized bone particles of step (f) by adding an aqueous ethanol solution and applying supersonic cavitation;
    (h) neutralizing the cleaned bone particles using a phosphate buffered saline (PBS);
    (i) steeping the neutralized bone particles of step (g) by adding a Radio Protective Stable Chemical (RSC) solution and applying supersonic cavitation, said RSC solution maintains osteoconductive and osteoinductive capabilities of said bone particle, protects osteogenesis induction factors, and prevents the bone particles from being rapidly dissolved or inactivated after being implanted in a living body;
    (j) cleaning the bone particles which have steeped in the RSC solution, using purified water and then drying the bone particles by removing the purified water; and
    (k) vacuum-freeze-drying the dried bone particles, thereby manufacturing a cancellous bone graft substitute.

2. The method of claim 1, wherein the steps of defatting, dehydrating, and disinfecting of the tissue and the step of cleaning the demineralized bone particles are performed in an 83% aqueous ethanol solution for about 30 minutes, and applying supersonic cavitation.

3. The method of claim 1, wherein the step of sterilizing and oxidizing the bone tissue using the peroxide is performed in a solution of peroxide of 3% for about 90 minutes, and applying supersonic cavitation.

4. The method of claim 1, wherein the step of demineralizing the bone particles having the hexahedral shapes is performed in a hydrochloric acid solution of 0.5N for 30 to 90 minutes, and applying supersonic cavitation.

5. The method of claim 1, wherein:
    the RSC solution, in which the neutralized bone tissue is steeped, has a composition of propylene glycol of 15% to 20%, dimethyl sulfoxide (DMSO) of 20% to 25%, mannitol of 1% to 5%, tetrahalose of 1% to 5%, and distilled water of 40% to 60%;
    the bone particles are steeped in the RSC solution in a constant-temperature water bath of 40° C. for 5 hours; and the bone particles are then placed in a freezer of 4° C. for 20 hours.

6. The method of claim 1, wherein:
    the RSC solution, in which the neutralized bone tissue is steeped, has a composition of glycine of 15% to 20%, stachyose of 20% to 25%, manitol of 1% to 5%, dextran of 1% to 5%, and distilled water of 40% to 60%;
    the bone particles are steeped in the RSC solution in a constant-temperature water bath of 40° C. for 5 hours; and
    the bone particles are placed in a freezer of 4° C. for 20 hours.

7. The method of claim 1, further comprising vacuum-wrapping, then vacuum-freeze-drying the cancellous bone graft substitute in a disinfected vial, capping the cancellous bone graft substitute with aluminum, and packing the cancellous bone graft substitute in a plastic box.

* * * * *

UNITED STATES PATENT AND TRADEMARK OFFICE
CERTIFICATE OF CORRECTION

| | | |
|---|---|---|
| PATENT NO. | : 8,409,623 B2 | Page 1 of 1 |
| APPLICATION NO. | : 12/359125 | |
| DATED | : April 2, 2013 | |
| INVENTOR(S) | : Y. B. Shim et al. | |

It is certified that error appears in the above-identified patent and that said Letters Patent is hereby corrected as shown below:

| COLUMN | LINE | ERROR |
|---|---|---|
| On the title page | | |
| Item 75 | | "Gyeonnggi-do" should read --Gyeonggi-do-- |
| Item 57 | 7 | "cabitation" should read --cavitation-- |
| Item 57 | 12 | "allogenetic" should read --allogeneic-- |
| In the claims | | |
| 8 | 29 | "manitol" should read --mannitol-- |

Signed and Sealed this
Twenty-third Day of February, 2016

Michelle K. Lee
*Director of the United States Patent and Trademark Office*